United States Patent
Dickow

(10) Patent No.: US 8,820,138 B2
(45) Date of Patent: Sep. 2, 2014

(54) SYSTEM FOR TAKING EXHAUST GAS SAMPLES FROM INTERNAL COMBUSTION ENGINES

(75) Inventor: Achim Dickow, Velbert (DE)

(73) Assignee: AVL Emission Test Systems GmbH, Neuss (DE)

( * ) Notice: Subject to any disclaimer, the term of this patent is extended or adjusted under 35 U.S.C. 154(b) by 260 days.

(21) Appl. No.: 13/259,148

(22) PCT Filed: Mar. 2, 2010

(86) PCT No.: PCT/EP2010/052588
§ 371 (c)(1), (2), (4) Date: Oct. 17, 2011

(87) PCT Pub. No.: WO2010/112286
PCT Pub. Date: Oct. 7, 2010

(65) Prior Publication Data
US 2012/0036836 A1    Feb. 16, 2012

(30) Foreign Application Priority Data

Mar. 31, 2009   (DE) .......................... 10 2009 015 188

(51) Int. Cl.
G01M 15/10   (2006.01)
G01M 15/02   (2006.01)
G01N 1/22    (2006.01)

(52) U.S. Cl.
CPC ..... G01M 15/102 (2013.01); G01N 2001/2264 (2013.01); G01N 1/2252 (2013.01); G01M 15/02 (2013.01)
USPC ...................................... 73/23.31

(58) Field of Classification Search
USPC ......... 73/23.31, 23.32, 23.33, 114.69, 114.71
See application file for complete search history.

(56) References Cited

U.S. PATENT DOCUMENTS

| 3,699,814 A | 10/1972 | Kaufman |
| 5,134,852 A | 8/1992 | Weeks |

(Continued)

FOREIGN PATENT DOCUMENTS

| CN | 201051058 Y | 4/2008 |
| DE | 2 236 972 A1 | 9/1973 |

(Continued)

OTHER PUBLICATIONS

"Agreement ECE-R 83, Regulation No. 83", Daimler AG, United Nations, Exhaust emissions, pp. 1-4, 110-122 (2008).

(Continued)

*Primary Examiner* — Hezron E Williams
*Assistant Examiner* — David Z Huang
(74) *Attorney, Agent, or Firm* — Norman B. Thot

(57) ABSTRACT

A system for taking an exhaust gas sample includes a first exhaust gas channel fluidically connected to a first exhaust gas source via a first exhaust gas inlet. A first air channel with a first air filter is configured to suck in ambient air. The first exhaust gas channel meets the first air channel in a first mixing zone, where a first exhaust gas is mixed with the ambient air to obtain a diluted exhaust gas/air mixture. A second exhaust gas channel is fluidically connected to a second exhaust gas source via a second exhaust gas inlet, and a second mixing zone. A control device and a measurement device are configured to respectively control and measure mass flows. The diluted exhaust gas/air mixture flows either from the first exhaust gas source or from the second exhaust gas source into the dilution tunnel and to at least one sampling probe.

22 Claims, 1 Drawing Sheet

(56) References Cited

U.S. PATENT DOCUMENTS

| | | |
|---|---|---|
| 5,337,595 A | 8/1994 | Lewis |
| 5,712,433 A | 1/1998 | Kojima |
| 5,746,176 A | 5/1998 | Damson et al. |
| 5,907,109 A | 5/1999 | Tedeschi |
| 7,340,940 B2 | 3/2008 | Kreft |
| 2002/0108451 A1 | 8/2002 | May et al. |
| 2002/0145080 A1 | 10/2002 | Renken et al. |
| 2004/0226354 A1 | 11/2004 | Schmidt |
| 2005/0112549 A1* | 5/2005 | Baumgardner et al. ........ 435/4 |
| 2005/0257605 A1* | 11/2005 | Colvin et al. ............. 73/118.1 |
| 2006/0042701 A1 | 3/2006 | Jansen |
| 2006/0231139 A1 | 10/2006 | Neumann |
| 2007/0113541 A1 | 5/2007 | Jankovic |
| 2007/0125188 A1 | 6/2007 | Kreft |
| 2008/0105031 A1* | 5/2008 | Arlt et al. ............... 73/23.32 |

FOREIGN PATENT DOCUMENTS

| | | |
|---|---|---|
| DE | 33 14 661 A1 | 10/1984 |
| DE | 44 20 193 A1 | 1/1996 |
| DE | 195 05 415 A1 | 8/1996 |
| DE | 196 31 922 A1 | 2/1997 |
| DE | 196 07 574 A1 | 9/1997 |
| DE | 693 15 463 T2 | 3/1998 |
| DE | 198 11 788 A1 | 9/1999 |
| DE | 100 00 653 A1 | 7/2001 |
| EP | 0 561 557 A1 | 9/1993 |
| EP | 1 477 801 A1 | 11/2004 |
| EP | 1 923 687 A1 | 5/2008 |
| JP | 11-200912 A | 7/1999 |
| JP | 2006-524126 A | 10/2006 |
| WO | WO 95/31636 A1 | 11/1995 |
| WO | WO 2006/087029 A1 | 8/2006 |
| WO | WO 2009/124327 A1 | 10/2009 |

OTHER PUBLICATIONS

"Regulations (EC) No. 715/2007", Official Journal of the European Union, pp. L 171/1-L 171/16 (Jun. 20, 2007).

"Regulation No 83, Revision 3", Official Journal of the European Union, pp. L 375/223-L 375/240, L 375/354-L 375/372 (2006).

"Acts Adopted by Bodies Created by International Agreements; Regulation No. 83", Official Journal of the European Union, pp. L 42/1-L 42/15, L 42/109-L 42/113 (2012).

"1958 Agreement, Proposal for Supplement 7 to the 05 series of amendments to Regulation No. 83", United Nations, Economic and Social Council, pp. 1-79 (2008).

F. Commiskey: "Advanced Emission Test Cell Facility in Ann Arbor", Readout HORIBA Technical Reports, No. 19, pp. 23-26 (Sep. 1999).

R. Omran et al.: "Genetic Algorithm for Dynamic Calibration of Engine's Actuators", SAE Technical Paper Series, General Emissions, pp. 1-7 (2007).

\* cited by examiner

US 8,820,138 B2

SYSTEM FOR TAKING EXHAUST GAS SAMPLES FROM INTERNAL COMBUSTION ENGINES

CROSS REFERENCE TO PRIOR APPLICATIONS

This application is a U.S. National Phase application under 35 U.S.C. §371 of International Application No. PCT/EP2010/052588, filed on Mar. 2, 2010 and which claims benefit to German Patent Application No. 10 2009 015 188.5, filed on Mar. 31, 2009. The International Application was published in German on Oct. 7, 2010 as WO 2010/112286 A1 under PCT Article 21(2).

FIELD

The present invention provides a system for taking exhaust gas samples from internal combustion engines, the system comprising a first exhaust gas channel which is fluidically connected to a first exhaust gas source via a first exhaust gas inlet, a first air channel into which ambient air can be sucked via a first air filter, a first mixing zone in which the first exhaust gas channel enters the first air channel, a dilution tunnel with an exhaust gas/air mixture flowing therethrough, at least one sampling probe, a pump for conveyance of the air and the exhaust gas, and means for control and measurement of the mass flows.

BACKGROUND

Various official regulations exist prescribing that the engines of automobiles must not exceed certain emission limit values, such as, for example, ECE Regulation R 83 for the European Community, or the Code of Federal Regulations No. 40 for the United States. For the most part, these standards prescribe, apart from limit values for emissions, the manner in which sampling is to be performed by use of systems with variable dilution that are provided for measurement of the emissions.

Systems of the above type are known, for example, under the term "CVS system" (constant volume sampling). In these systems, the exhaust gas is always admixed with such a quantity of air that a constant total volume flow of the air/exhaust gas mixture is generated. The samples, which in these systems are taken in bags, are subsequently be analyzed with respect to their pollutant content. The carbon dioxide, carbon monoxide, carbon hydride and nitrogen oxide contents are, for example, measured. While a particle measurement up to now had to be performed only for diesel engines, this measurement will in the future be obligatory also for Otto engines with direct injection.

An advanced variant of a CVS system for taking exhaust gas samples is described in DE 693 15 463 T2. This system comprises an exhaust gas inlet and an air inlet with an air filter upstream thereof. Via a controlled pump, the two gas flows are sucked into a following mixing zone from which they will proceed, while being mixed as homogeneously as possible, into a dilution tunnel. In the dilution tunnel, at a sufficient distance from the mixing zone, a subsonic Venturi nozzle is arranged which is connected to a channel for taking a sample therefrom, the gas flow through this channel being generated by a second pump. In the further course of the dilution tunnel upstream of the conveying pump, the dilution channel is narrowing again in the form of a subsonic Venturi nozzle. Via these Venturi nozzles, the mass flow velocities are detected which are set to be proportionate to each other. The pressure or temperature of the mixed gas are detected via various further sensors and communicated to a control unit by which the proportionality of the mass flow velocities at the two Venturi nozzles and an identical effective pressure shall be safeguarded.

Such a system, also known as CVS systems, is not, however, suited for use as a system for sampling exhaust gas in Otto and diesel engines because one would have to expect particle and carbon hydride deposits to occur in the region of the conduit system, which would distort a subsequent measurement.

The present state of developments therefore resides in the use of two parallel dilution tunnels with two sampling probes wherein the required conveying speed is generated only via a common conveying pump.

Even though DE 195 05 415 A1 describes an exhaust gas test stand wherein two roller-type test stands are connected to a single CVS system, DE 195 05 415 A1 merely provides switching over the exhaust gas inlet, thus making it impossible to use one branch for diesel engines and one branch for Otto engines because, particle and HC residues would then be expected in the area of the mixing zone.

SUMMARY

An aspect of the present invention is to develop a system which is adapted to comply with legal regulations while performing a reliable and correct sampling, for example, for particle measurement, for both diesel and Otto engines. An additional, alternative aspect of the present invention is to same available space and reducing production costs.

In an embodiment, the present invention provides a system for taking an exhaust gas sample from an internal combustion engine which includes a first exhaust gas channel fluidically connected to a first exhaust gas source for a first exhaust gas via a first exhaust gas inlet. A first air channel with a first air filter is disposed therein, the first air channel being configured to suck in ambient air. The first exhaust gas channel meets the first air channel in a first mixing zone, the first mixing zone being configured to mix the first exhaust gas with the ambient air so as to obtain a diluted exhaust gas/air mixture. A second exhaust gas channel is fluidically connected to a second exhaust gas source for a second exhaust gas via a second exhaust gas inlet, and a second mixing zone. A dilution tunnel is configured to have the diluted exhaust gas/air mixture flow therethrough. At least one sampling probe. A pump is configured to convey the diluted exhaust gas/air mixture. A control device and a measurement device are configured to respectively control and measure mass flows. The diluted exhaust gas/air mixture is configured to flow either from the first exhaust gas source or from the second exhaust gas source into the dilution tunnel and to the at least one sampling probe. Such a configuration allows, for example, both the dilution tunnel and the sampling probe as well as the conveying pump to be used for both measurements. This in turn results in a reduction of the production and assembly costs, and of the space required therefor.

BRIEF DESCRIPTION OF THE DRAWINGS

The present invention is described in greater detail below on the basis of embodiments and of the drawings in which.

DETAILED DESCRIPTION

Figure 1:
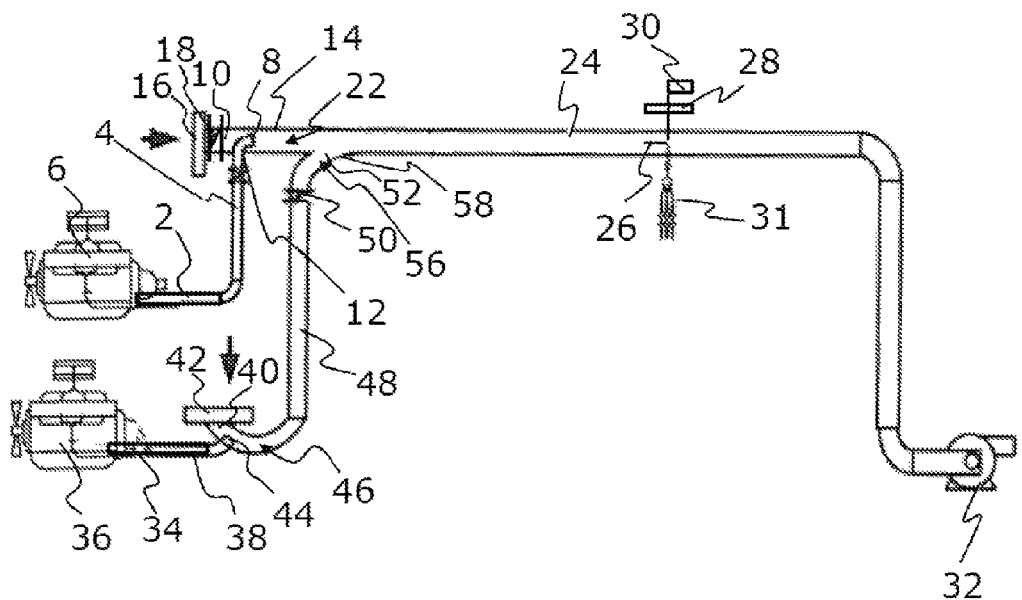
FIG. 1 is a schematic view of a system of the present invention for the taking of exhaust gas samples.

In an embodiment of the present invention, within the second mixing zone, the second exhaust gas channel enters into a second air channel into which ambient air can be sucked via a second air filter. It is thereby avoided that deposits of the first mixing zone can be entrained, through the first air channel and respectively the first mixing zone, into the mixed flow of the second path and thus adulterate the sample which is to be taken.

A good mixing is obtained if the first mixing zone is formed by a tube end of the first exhaust gas channel that is arranged substantially concentrically in the first air channel. A representative sampling is thereby rendered possible in this manner.

In an embodiment of the present invention, an annular orifice is arranged in the first mixing zone, immediately behind the tube end of the first exhaust gas channel. The orifice provides that the velocity of the air is increased in the region of the mixing site in the region adjacent to the first suction tube, thus providing additional homogenization.

In an embodiment of the present invention, a mixing tube enters the dilution tunnel behind the first mixing zone when seen in flow direction, said mixing tube being arranged behind the second mixing zone when seen in flow direction, wherein the dilution tunnel comprises, in its boundary wall, an orifice which is closed by the mixing tube and at which the mixing tube terminates. Such a feed of the second gas flow into the dilution tunnel reliably avoids influencing the first gas flow by existing fixtures or the like.

In order to avoid air from being sucked from the respective non-used air channel or exhaust gas channel, a respective control flap can be arranged in the mixing tube and between the first air filter and the opening of the mixing tube.

The end of the mixing tube can, for example, be arranged obliquely in the flow direction toward the dilution tunnel. This allows for a largely pressure-loss-free feed-in from the mixing tube into the dilution tunnel. Edges which, when using the first exhaust gas path, would lead to turbulences during the flow past the feed-in site are also reliably avoided. Flow losses are thus avoided in both paths.

In an embodiment of the present invention, the distance between the tube end of the first exhaust gas channel and the opening of the dilution tunnel toward the mixing tube is 0.5 times to 5 times, for example, 1.5 to 2 times the diameter of the mixing tube. Such ratios have been found to yield good results due to the largely reduced mutual influencing of the two exhaust gas paths.

An additional improvement of the homogeneity of the flows can be obtained if the angle between the center axes of the dilution tunnel and of the mixing tube is 10° to 50°, for example, 20° to 30°.

The first exhaust gas source can, for example, be a diesel engine and the second exhaust gas source an Otto engine since the entrance passage into the dilution tunnel via the first exhaust gas path is shorter than the passage via the second exhaust gas path, and since heat losses in the diesel exhaust gas must be avoided to the largest extent possible.

A system is thus provided for taking exhaust gas samples from internal combustion machines which is adapted to take particle samples from diesel and Otto engines via a common dilution tunnel and a common sampling probe. The complexity of the design and thus the production and assembly costs are reduced while, at the same time, a largely pressure-loss-free mixing and conveyance as well as a representative sampling are safeguarded.

Under reference to FIG. 1, the system of the present invention for the taking of exhaust gas samples from internal combustion engines for diesel and Otto engines comprises a first exhaust gas inlet 2 via which a first exhaust gas channel 4 is fluidically connected to an exhaust gas source 6 formed by the diesel engine of an automobile.

This exhaust gas channel 4 has a tube end 8 which concentrically enters a first air channel 10. For this purpose, the latter comprises an opening 12 in its boundary wall 14, with the exhaust gas channel 4 extending vertically therethrough into the air channel 10. For entering the air channel 10 concentrically, exhaust gas channel 4 is formed with a 90° deflection.

At the beginning of air channel 10, a first air filter 16, normally comprising three filters, is arranged thereon for suctional intake of air into air channel 10. Behind the air filter, a first control flap 18 is arranged for closing the air channel 10, if necessary. The deflection of exhaust gas channel 4 is realized in such a manner that the open tube end 8 is directed toward the side opposite to air filter 16 so that the air flow and the exhaust air flow have a common flow direction at the tube end 8.

Figure 2:
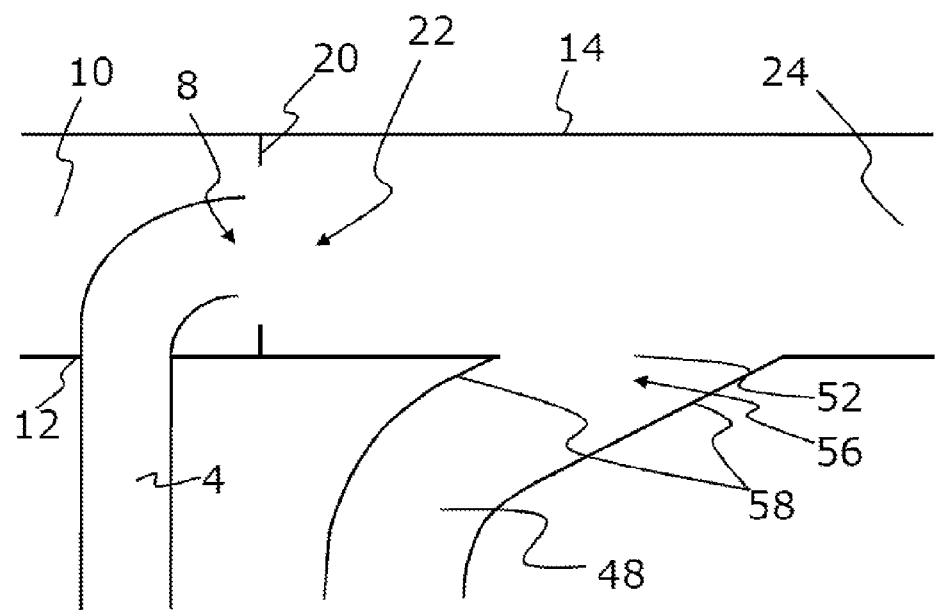
FIG. 2 is an enlarged view of a detail of the system in the area of the mixing zones.

As evident particularly from FIG. 2, an annular orifice 20 is arranged, when seen in flow direction, immediately behind the tube end 8 at a boundary wall 14 of air channel 10, whereby the cross section of the air channel available for free flow is reduced so that the flow speed will be increased and turbulences will be generated. By these turbulences, which occur, with reduced strength, also due to reduced cross section caused by the interior exhaust channel 4, a homogenous mixing of the exhaust gas with the air will be achieved in a following first mixing zone 22. This mixing zone can be arranged several meters away from the exhaust gas source 6.

Said mixing zone 22 is followed by a dilution tunnel 24 where a uniform flow of the exhaust gas/air mixture prevails. Within dilution tunnel 24, a sampling probe 26 for taking a sample from the mixed flow is arranged centrally relatively to the central axis. The sample flow taken via said sampling probe 26 will be supplied to a heatable filter 28 of a flame ionization detector by which the carbon hydrides in the exhaust gas are determined, and will then be selectively supplied to at least one sample bag 30. Additionally, by use of at least sampling probe 26, the mixed flow will be guided via a filter unit 31 for determining the particle emissions. Conveyance of the analysis flows is respectively performed by separate pumps, not illustrated.

The rest of the mixed gas flow will proceed from the dilution tunnel 24 to a controllable conveying pump 32 provided for generating a sufficient pressure for conveyance of the air and of the exhaust gas. There, the mixed gas flow will be discharged. Apart from the provision of a controlled conveying pump 32, it is also possible to arrange, upstream the conveying pump, a control flap or a supercritical nozzle for setting the required conveying flow.

In addition to the illustrated sampling arrangement, the system can also comprise an additional sampling device for an exhaust gas sample, by which the contents of nitrogen oxide, carbon dioxide and carbon monoxide can be detected.

According to the present invention, the system comprises, in addition to the known aggregates for measurement of the HC emissions and particle emissions at the diesel engine, a second exhaust gas inlet 34 which can be connected to a second exhaust gas source 36 in the form of an Otto engine, particularly an Otto engine with direct injection, which in the future will also be subject to a requirement for particle measurement, apart from the HC emission measurement.

A second exhaust gas channel 38 is fluidically connected to the exhaust gas source 36 via the second exhaust gas inlet 34. In the manner already described in the context of the first exhaust gas path, said channel enters into a second air channel 40 at whose entrance, in turn, a second air filter 42 is arranged for preventing the intrusion of pollutants from the ambient air into air channel 40.

The tube end 44 of the second exhaust gas channel 38 is followed by a second mixing zone 46 wherein the mixed flow of exhaust gas/air will be homogenized. This second mixing zone 46 is arranged as closely as possible to second exhaust gas source 36 and is a part of a mixing tube 48 by which the mixed gas flow will be fed into the dilution tunnel 24. For optionally closing the cross section of said mixing tube 48, a second control valve/flap 50 is arranged in mixing tube 48.

The mixing tube 48 terminates in an opening 52 of the boundary wall 14 of dilution tunnel 24 into which the air channel 10 merges. The central axis of the end 56 of mixing tube 48 as well as the boundary walls 58 extending substantially parallel thereto, are arranged at an angle of about 25° relative to the central axis and respectively the boundary walls 14 of dilution tunnel 24, notably in such a manner that the flow from the mixing tube 48 has to be deflected merely by this angle for entering into dilution tunnel 24. Angles can, for example, be from 20° to 30°.

The distance between the tube end 8 of first exhaust gas channel 4 and the portion of opening 52 closest thereto is about 240 mm in case of a 150 mm tube diameter of mixing tube 48 and thus is about 1.6 times the tube diameter. The distance can, for example, be selected to be 1.5 to 2 times the tube diameter. By these dimensions, pressure losses will be largely excluded.

The exhaust gas/air mixture will further flow through dilution tunnel 24 to sampling probe 26 and respectively to conveying pump 32 in the same manner as the exhaust gas/air mixture from the first mixing zone 22 so that also a corresponding analysis can take place.

Selectively, via the first mixing zone 22, the diesel exhaust gas/air mixture or, via the second mixing zone 46, the Otto-engine exhaust gas/air mixture will be conveyed for sampling via dilution tunnel 24. The respective non-used system will be fluidically separated from dilution tunnel 24 by closing the first control valve/flap 18 or the second control valve/flap 50 so that, as far as possible, no leakage air can be sucked in via the non-used path.

Due to the sufficient distance between the tube end 8 and the opening 52, it is effected that, when using the first exhaust gas path, a homogenous flow will be generated before this opening 52 in the first mixing zone 22 prior to reaching the opening 52, so that practically no additional turbulence will occur. No deposits are further expected in this region because the second mixing zone 46, where most deposits could occur, is arranged remote from the feed-in site. A largely homogenous flow further exists in this region also for the second exhaust gas path. The feed-in site will therefore neither cause pressure losses nor impair the measurement results due to existing residues from the second exhaust gas path.

The same also applies for the use of the second exhaust gas path. This path leads into the dilution tunnel 24 only at a sufficient distance behind the feed-in site and respectively the mixing zone 22 of the first exhaust gas path, so that no particles from the first exhaust gas path will be entrained by the exhaust gas flow. Adulteration of the measurement results is therefore largely excluded here because no residues of diesel exhaust gas are expected in this region. Since, when using the second exhaust gas path, there will further exist no flow at the first feed-in point due to closure of control valve/flap 18, it is also expected that no residues will be entrained from the mixing zone.

Mutual influencing of the two gas flows is thus avoided. Instead, by the above system, the critical regions of the two paths are separated from each other. The system is thus suited for measurement of the exhaust gas of diesel and Otto engines and, in regard to the latter, especially of Otto engines with direct injection, without the need to use various different diluting agents or sampling probes. In correspondence thereto, the space requirement is reduced and the technical expenditure is distinctly decreased so that production and assembly costs are lowered. This can be accomplished, for example, by the use of identical components such as, for example, dilution tunnel, sampling probe, filters, but also peripheral devices such as control and measurement devices for both systems.

It is also noted that the exhaust gas will be diluted at a defined ratio to the ambient air. Sampling will be performed respectively proportionately to the throughflow through the pump. For this purpose, sampling systems with variable dilution and displacement pump are known, as are dilution systems with a critically traversed Venturi tube, as described, for example, in ECE Regulation R 83. The arrangement of the flow controllers, the valves, and of the flow, pressure and temperature measurement devices used in these systems is also known, and is different in dependence of the system used, so that these control options are assumed to be available to a person of skill in the art. The present invention is suited for all of these types of sampling. The features necessary for the present invention are independent from the system used.

The present invention is not limited to embodiments described herein; reference should be had to the appended claims.

The invention claimed is:

1. A system for taking an exhaust gas sample from an internal combustion engine, the system comprising:
    a first exhaust gas channel fluidically connected to a first exhaust gas source for a first exhaust gas via a first exhaust gas inlet;
    a first air channel with a first air filter disposed therein, the first air channel being configured to suck in ambient air;
    a first mixing zone in which the first exhaust gas channel meets the first air channel, the first mixing zone being configured to mix the first exhaust gas with the ambient air so as to obtain a first exhaust gas/air mixture;
    a second exhaust gas channel fluidically connected to a second exhaust gas source for a second exhaust gas via a second exhaust gas inlet;
    a second mixing zone in which the second exhaust gas channel meets a second air channel configured to suck in ambient air, the second mixing zone being configured to mix the second exhaust gas with the ambient air so as to obtain a second exhaust gas/air mixture;
    a dilution tunnel configured to have the first exhaust gas/air mixture or the second exhaust gas/air mixture flow therethrough;
    at least one sampling probe configured to take particle samples arranged in the dilution tunnel;
    a pump configured to convey the first exhaust gas/air mixture or the second exhaust gas/air mixture; and
    a control device and a measurement device configured to respectively control and measure mass flows;
    wherein the first exhaust gas/air mixture and the second exhaust gas/air mixture are each configured to flow into the dilution tunnel and to the at least one sampling probe, wherein, either the first exhaust gas/air mixture or the second exhaust gas/air mixture flow into the dilution tunnel and to the at least one sampling probe at any time.

2. The system as recited in claim 1, wherein the second air channel comprises a second air filter.

3. The system as recited in claim 1, wherein the first mixing zone is formed by a tube end of the first exhaust gas channel, the tube end being arranged substantially concentrically in the first air channel.

4. The system as recited in claim 3, further comprising an annular orifice arranged in the first mixing zone directly downstream of the tube end of the first exhaust gas channel.

5. The system as recited in claim 1, further comprising a mixing tube arranged to enter the dilution tunnel downstream of the first mixing zone, the mixing tube also being arranged downstream of the second mixing zone, wherein the dilution tunnel has an opening in its boundary wall, and the mixing tube ends at and closes the opening of the boundary wall.

6. The system as recited in claim 5, further comprising a control flap respectively arranged in the mixing tube and between the first air filter and where the mixing tube meets the dilution tunnel.

7. The system as recited in claim 5, wherein the mixing tube has an end, wherein the end is arranged diagonally in a direction of flow towards the dilution tunnel.

8. The system as recited in claim 7, wherein a distance between a tube end of the first exhaust gas channel and the opening of the dilution tunnel to the mixing tube is 0.5 times to 5 times a diameter of the mixing tube.

9. The system as recited in claim 8, wherein the distance is 1.5 to 2 times the diameter of the mixing tube.

10. The system as recited in claim 9, wherein an angle between a center axis of the dilution tunnel and a center axis of the mixing tube is 10° to 50°.

11. The system as recited in claim 10, wherein the angle is 20° to 30°.

12. The system as recited in claim 5, wherein the mixing tube has an end, wherein the end is arranged diagonally in a direction of flow towards the dilution tunnel.

13. The system for as recited in claim 12, wherein a distance between a tube end of the first exhaust gas channel and the opening of the dilution tunnel to the mixing tube is 0.5 times to 5 times a diameter of the mixing tube.

14. The system for as recited in claim 13, wherein the distance is 1.5 to 2 times the diameter of the mixing tube.

15. The system as recited in claim 14, wherein an angle between a center axis of the dilution tunnel and a center axis of the mixing tube is 10° to 50°.

16. The system as recited in claim 15, wherein the angle is 20° to 30°.

17. The system as recited in claim 1, wherein the first exhaust gas source is a diesel engine and the second exhaust gas source is an Otto engine.

18. A system for taking an exhaust gas sample from an internal combustion engine, the system comprising:
a first exhaust gas channel fluidically connected to a first exhaust gas source for a first exhaust gas via a first exhaust gas inlet;
a first air channel with a first air filter disposed therein, the first air channel being configured to suck in ambient air;
a first mixing zone in which the first exhaust gas channel meets the first air channel, the first mixing zone being configured to mix the first exhaust gas with the ambient air so as to obtain a first exhaust gas/air mixture;
a second exhaust gas channel fluidically connected to a second exhaust gas source for a second exhaust gas via a second exhaust gas inlet;
a second mixing zone in which the second exhaust gas channel meets a second air channel configured to suck in ambient air, the second mixing zone being configured to mix the second exhaust gas with the ambient air so as to obtain a second exhaust gas/air mixture;
a dilution tunnel configured to have the first exhaust gas/air mixture or the second exhaust/gas mixture flow therethrough;
a mixing tube arranged to enter the dilution tunnel downstream of the first mixing zone, the mixing tube also being arranged downstream of the second mixing zone, wherein the dilution tunnel has an opening in its boundary wall, and the mixing tube ends at and closes the opening of the boundary wall;
at least one sampling probe configured to take particle samples arranged in the dilution tunnel;
a control flap respectively arranged in the mixing tube and between the first air filter and where the mixing tube meets the dilution tunnel, the control flap being configured so that the first exhaust gas/air mixture and the second exhaust gas/air mixture each flow into the dilution tunnel and to the at least one sampling probe, wherein, either the first exhaust gas/air mixture or the second exhaust gas/air mixture flow into the dilution tunnel and to the at least one sampling probe at any time;
a pump configured to convey the first exhaust gas/air mixture or the second exhaust gas/air mixture; and
a control device and a measurement device configured to respectively control and measure mass flows.

19. The system as recited in claim 18, wherein the second air channel comprises a second air filter.

20. The system as recited in claim 18, wherein the first mixing zone is formed by a tube end of the first exhaust gas channel, the tube end being arranged substantially concentrically in the first air channel.

21. The system as recited in claim 20, further comprising an annular orifice arranged in the first mixing zone directly downstream of the tube end of the first exhaust gas channel.

22. The system as recited in claim 18, wherein the first exhaust gas source is a diesel engine and the second exhaust gas source is an Otto engine.

* * * * *